United States Patent [19]

Wojtowicz

[11] Patent Number: 4,599,411

[45] Date of Patent: Jul. 8, 1986

[54] PROCESS FOR THE PRODUCTION OF ALKALI METAL SALTS OF DICHLOROISOCYANURIC ACID

[75] Inventor: John A. Wojtowicz, Cheshire, Conn.

[73] Assignee: Olin Corporation, Cheshire, Conn.

[21] Appl. No.: 740,662

[22] Filed: Jun. 3, 1985

[51] Int. Cl.$^4$ ............................................. C07D 251/36
[52] U.S. Cl. ...................................................... 544/190
[58] Field of Search .......................................... 544/190

[56] References Cited

U.S. PATENT DOCUMENTS 4,389,318  6/1983  Wojtowicz ........................ 210/755
4,898,223  8/1975  Wojtowicz ........................ 260/248 C Primary Examiner—John M. Ford
Attorney, Agent, or Firm—James B. Haglind; Thomas P. O'Day

[57] ABSTRACT

A process for producing a sodium compound comprises admixing trichloroisocyanuric acid, cyanuric acid, and sodium bicarbonate to form a homogeneous mixture. The homogeneous mixture is reacted with water and a sodium dichloroisocyanurate compound recovered. The novel process minimizes the cost of raw materials and maximizes the available chlorine present in the reaction mixture.

11 Claims, No Drawings

PROCESS FOR THE PRODUCTION OF ALKALI METAL SALTS OF DICHLOROISOCYANURIC ACID

This invention relates to a process for the production of alkali metal salts of dichloroisocyanuric acid. The salts are well known products used in laundry, bleaching and sanitizing applications.

It is known to produce alkali metal salts of dichloroisocyanuric acid by reacting trichloroisocyanuric acid with a salt of cyanuric acid. One method of producing sodium dichloroisocyanurate is described in U.S. Pat. No. 3,035,057 issued May 15, 1962, to W. F. Symes. In this method, trichloroisocyanuric acid is reacted with trisodium isocyanurate in an aqueous medium maintained at a pH of 5.0 to 7.5 at a temperature in the range of 0° to 50° C. Following filtering and drying, the sodium dichloroisocyanurate or its hydrate is recovered.

In another method, described in U.S. Pat. No. 3,898,223, issued Aug. 5, 1975, to J. A. Wojtowicz, trichloroisocyanuric acid is reacted with sodium bicarbonate in the presence of water at ambient temperatures to produce sodium dichloroisocyanurate. Also produced in this method is hypochlorous acid which is evolved from the reaction mixture.

Dry mixtures of trichloroisocyanuric acid, cyanuric acid, and sodium bicarbonate were prepared in U.S. Pat. No. 4,389,318, issued June 21, 1983, to J. A. Wojtowicz, which were compressed for use in water bodies such as swimming pools. The dry mixtures, having a moisture content below about 0.2 percent, when added to the water body produce in situ an aqueous solution of sodium dichloroisocyanurate.

There is need, however, for a process which produces sodium dichloroisocyanurate granules using reduced amounts of chlorine and without the loss of available chlorine from the reaction mixture.

It is an object of the present invention to provide a process for the production of a sodium dichloroisocyanurate compound in which the loss of available chlorine is minimized.

Another object of the present invention is to provide a process for the production of a sodium dichloroisocyanurate compound having reduced costs for raw materials.

These and other objects of the present invention are accomplished in a process for the production of a sodium dichloroisocyanurate compound which comprises admixing trichloroisocyanuric acid, cyanuric acid, and sodium bicarbonate to form a homogeneous mixture, reacting said homogeneous mixture with water, and recovering said sodium dichloroisocyanurate compound.

More in detail, the novel process of the present invention uses trichloroisocyanuric acid (TCCA) which is a commercially available compound having an available chlorine concentration in the range of from about 89 to about 91.5 percent. Trichloroisocyanuric acid is produced by known processes such as those described, for example, in U.S. Pat. Nos. 3,757,018, issued Sept. 4, 1973, to R. N. Mesiah; 3,810,982, issued May 14, 1974, to R. N. Mesiah; 3,835,134, issued Sept. 10, 1974, to H. W. Schiessl et al; and 3,835,135, issued Sept. 10, 1974, to D. L. Sawhill.

The second required ingredient of the novel composition is commercially available sodium bicarbonate.

Cyanuric acid, the third required ingredient, is an article of commerce which is preferably reduced in particle size prior to its addition to the reaction mixture. Granular cyanuric acid is reduced by known means such as milling or grinding to particle sizes of less than about 100 microns, for example, from about 50 to about 75 microns.

TCCA, sodium bicarbonate, and cyanuric acid are blended together to produce a homogeneous mixture.

To produce a sodium dichloroisocyanurate compound having an available chlorine concentration of at least 50 percent, the homogeneous mixture comprises a molar ratio of sodium bicarbonate to TCCA in the range from about 2:1 to about 1:1 and preferably from about 1.4:1 to about 1.6:1, and a molar ratio of TCCA to cyanuric acid of from about 1.5:1 to 2.5:1 and preferably from about 1.8:1 to about 2.2:1.

To facilitate the handling of the homogeneous mixture, it may be granulated by known means such as roll compaction, followed by crushing and screening. Water, under controlled conditions, is added to the homogeneous mixture to produce a hydrated sodium dichloroisocyanurate compound, such as sodium dichloroisocyanurate dihydrate. The overall reaction for producing sodium dichloroisocyanurate dihydrate is represented by the following equation:

$$2Cl_3C_3N_3O_3 + H_3C_3N_3O_3 + 3NaHCO_3 + 3H_2O \rightarrow 3\text{-}NaCl_2C_3N_3O_3 \cdot 2H_2O + 3CO_2. \qquad (1)$$

Controlled addition of the water permits the water to be uniformly admixed with the trichloroisocyanuric acid, cyanuric acid, and sodium bicarbonate blend. This can be accomplished, for example, by employing agitation means which commix the water and the solids while permitting the rapid release of the carbon dioxide gas formed.

In a preferred embodiment, water is added in the form of droplets or in the vapor phase as steam. Suitable amounts of water are added to assure that the reaction goes to completion, for example, from about 6 to about 25 percent, and preferably from about 9 to about 22 percent by weight of the homogeneous mixture.

As the reaction between the homogeneous mixture and water is endothermic, heat is provided to maintain the reaction temperature in the range of from about 5° to about 60° C. Heat is required as the release of carbon dioxide results in evaporative cooling of the reaction mixture.

In a preferred embodiment, steam is used to provide the water needed as well as the heat required to maintain the desired temperature of the reaction mixture.

The reaction is conducted for a period of time sufficient to evolve all of the carbon dioxide produced.

The sodium dichloroisocyanurate compound produced initially is the dihydrate. This compound can be used as produced or dried by known means to provide hydrated sodium dichloroisocyanurate having reduced amounts of water of hydration or anhydrous sodium dichloroisocyanurate. Compounds produced by the novel process of the present invention have an available chlorine concentration in the range of from about 50 to about 64, and preferably from about 54 to about 63 percent.

The novel process of the present invention produces a sodium dichloroisocyanurate compound while minimizing the cost of raw materials such as trichloroisocyanuric acid. Maximum use is made of the available chlorine present in the reaction mixture and the use of scrubbers or other chlorine-recovery means is not required. The process is free of by-products which contaminate the sodium dichloroisocyanurate compound produced. Recovery of the product is greatly facilitated and purification, not normally required, is simplified.

The process is further illustrated by the following examples with no intention of being limited thereby. All parts and percentages are by weight unless otherwise indicated.

EXAMPLE 1

Commercial trichloroisocyanuric acid (58.1 g., 90.7% avail. Cl.), sodium bicarbonate (30.63 g.), and micropulverized cyanuric acid (14.55 g. particle size range 95% less than 200 mesh; 74 microns) were admixed in a reactor equipped with a stirrer. Water (22.0 g., 21% by weight of the mixture) was added dropwise to the well-agitated reaction mixture. The reactor was maintained at room temperature by means of a water bath. Carbon dioxide liberated from the reaction mixture was scrubbed in a caustic soda solution. Analysis of the scrubber solution for $HCO_3^-$ and $CO_3^{-2}$ indicated the reaction had gone essentially to completion. The air dried sodium dichloroisocyanurate dihydrate product (93.4 g.) had the following analysis: available chlorine 55.2%; water 13.8%; assay 99.4%.

EXAMPLE 2

Trichloroisocyanuric acid (7,176 g, 90% av. Cl), cyanuric acid (1,981 g) and sodium bicarbonate (3,882 g) in powder form were blended batchwise in a V-blender for 1 hour. The powdered blend was granulated in a compactor/granulator and the granules screened to provide a granulated mixture having the following particle size distribution:

| Mesh | Microns | % |
|---|---|---|
| +16 | +1,190 | 3.0 |
| −16/+20 | −1,190/+840 | 16.3 |
| −20/+30 | −840/+540 | 16.0 |
| −30/+50 | −590/+297 | 28.5 |
| −50/+70 | −297/+210 | 10.1 |
| −70 | −210 | 23.4 |

To 282.0 g of the above mixture in a stirred flask was added 20.0 g (7% by weight) of water over about 30 mins. After about 40 mins. at room temperature, the reaction mixture was heated at 40°–60° C. for 1.8 hours. The product weighed 255.9 g and contained 54.1% av. Cl and 11.2% water and represented about 95% conversion to hydrated sodium dichloroisocyanurate.

EXAMPLES 3–6

The granulated mixture of EXAMPLE 1 was sieved to provide granules in the −20/+70 mesh (−840/+210 microns) range. Four portions (28.2 g each) of this sieved mixture were placed in vessels and varying amounts of water added. The water was thoroughly admixed with the granular mixture and the products allowed to dry overnight. The available chlorine concentration and the water content was determined. The results are provided in Table 1 below.

TABLE 1

Preparation of Hydrated Sodium Dichloroisocyanurate

| | Granular TCCA/CA NaHCO$_3$ Mixture g | H$_2$O g | Air-Dried Product g | Analysis Av. Cl. % | H$_2$O % | Assay % |
|---|---|---|---|---|---|---|
| Example 3 | 28.2 | 1.8 | 26.26 | 52.62 | 10.68 | 92.30 |
| Example 4 | " | 1.9 | | 52.92 | 11.06 | 93.14 |
| Example 5 | " | 2.7 | 25.69 | 53.31 | 12.95 | 95.64 |
| Example 6 | " | 3.6 | 25.49 | 53.58 | 13.55 | 96.66 |

EXAMPLES 7–10

The procedure of EXAMPLES 2–5 was repeated using a blended mixture of TCCA, CA and NaHCO$_3$ in powdered form. The results are given in Table 2 below.

TABLE 2

Preparation of Hydrated Sodium Dichloroisocyanurate

| | Powdered TCCA/CA/ NaHCO$_3$ Mixture g | Water g | % Excess | Air-Dried Product g | Analysis Av. Cl. % | Assay % | H$_2$O % |
|---|---|---|---|---|---|---|---|
| Example 7 | 28.2 | 1.8 | 0 | 27.32 | 52.43 | 88.04 | 6.72 |
| Example 8 | " | 2.7 | 50 | 26.51 | 53.05 | 92.36 | 10.07 |
| Example 9 | " | 3.6 | 100 | 25.91 | 54.15 | 96.84 | 12.85 |
| Example 10 | " | 6.0 | 233 | 25.38 | 54.59 | 98.46 | 13.78 |

EXAMPLE 11

TCCA 464.8 g, CA 129.1 g, and $NaHCO_3$ 252.0 g in powder form were blended in a V-mixer. The mixture was pressed into tablets (diameter 3 inches, thickness ⅛ inch, weight 30 g) using a pressure of about 6,500 psi. The tablets were crushed and sieved to provide a granular product (469.8 g) passing through a 16 mesh (1190 microns) screen, but being retained on a 50 mesh (297 microns) screen. The granular product (200 g) was put into a Teflon coated 316SS rotary drum fitted with internal flights. The drum was rotated at 54 rpm to generate a cascade of particles which were coated with a fine spray of water (10.5 g) from an atomizer. After heating for 30 minutes at 40° C., the product (188.4 g) had an av. Cl of 53.1% indicating incomplete conversion. An additional 6.8 g of water was added and the product heated for 30 mins. at 40° C. and 30 mins. at 50° C. giving 177.6 g of product containing 55.0% av. Cl. and 9.5% $H_2O$ indicating a conversion of about 95% to hydrated sodium dichloroisocyanurate.

What is claimed is:

1. A process for producing a sodium dichloroisocyanurate compound which comprises admixing trichloroisocyanuric, cyanuric acid, and sodium bicarbonate to form a homogeneous mixture, reacting said homogeneous mixture with water in the form of droplets or steam, and recovering said sodium dichloroisocyanurate compound.

2. The process of claim 1 in which said water is added in amounts of from about 6 to about 25 percent by weight of said homogeneous mixture.

3. The process of claim 2 in which said reaction is conducted at temperatures in the range of from about 5° to about 60° C.

4. The process of claim 3 in which the particle size of cyanuric acid is less than about 100 microns.

5. The process of claim 4 in which the molar ratio of trichloroisocyanuric acid to cyanuric acid is from about 1.5:1 to about 2.5:1.

6. The process of claim 3 in which said homogeneous reaction mixture is reacted with water in droplet form.

7. The process of claim 6 in which said reaction is agitated to permit rapid release of carbon dioxide gas formed.

8. The process of claim 3 in which said water in said reaction is steam.

9. The process of claim 4 in which said water is added to said homogeneous mixture in a fluidized bed reaction zone.

10. The process of claim 4 in which said homogeneous mixture is granulated prior to said reaction with water.

11. The process of claim 4 in which said sodium dichloroisocyanurate compound is anhydrous sodium dichloroisocyanurate or hydrated sodium dichloroisocyanurate.

* * * * *